(12) United States Patent
Riedel et al.

(10) Patent No.: US 10,786,627 B2
(45) Date of Patent: Sep. 29, 2020

(54) DEVICE FOR ATTACHMENT TO A DRUG DELIVERY DEVICE

(71) Applicant: SANOFI-AVENTIS DEUTSCHLAND GMBH, Frankfurt am Main (DE)

(72) Inventors: Stephan Riedel, Frankfurt am Main (DE); Alexander Allerdings, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 73 days.

(21) Appl. No.: 15/579,801

(22) PCT Filed: Jun. 10, 2016

(86) PCT No.: PCT/EP2016/063323
§ 371 (c)(1),
(2) Date: Dec. 5, 2017

(87) PCT Pub. No.: WO2016/198617
PCT Pub. Date: Dec. 15, 2016

(65) Prior Publication Data
US 2018/0353694 A1 Dec. 13, 2018

(30) Foreign Application Priority Data
Jun. 10, 2015 (EP) .................................... 15171308

(51) Int. Cl.
*A61M 5/24* (2006.01)
*A61M 5/315* (2006.01)
(Continued)

(52) U.S. Cl.
CPC ............ *A61M 5/24* (2013.01); *A61M 5/3155* (2013.01); *G06K 9/6203* (2013.01);
(Continued)

(58) Field of Classification Search
None
See application file for complete search history.

(56) References Cited

U.S. PATENT DOCUMENTS

2006/0188159 A1  8/2006  Shiyama
2011/0178461 A1*  7/2011  Chong .................. A61M 5/158
                                                                  604/151
(Continued)

FOREIGN PATENT DOCUMENTS

CN       104048739 B  *  4/2017  ........ A61M 5/14248
EP          3103491         12/2016
(Continued)

OTHER PUBLICATIONS

International Search Report and Written Opinion in International Application No. PCT/EP2016/063323, dated Aug. 22, 2016, 12 pages.
(Continued)

*Primary Examiner* — Jiangeng Sun
(74) *Attorney, Agent, or Firm* — Fish & Richardson P.C.

(57) ABSTRACT

Apparatus configured to assist a user in correctly positioning the apparatus on a drug delivery device, the apparatus comprising: attachment means for attaching the apparatus to the drug delivery device; an imaging arrangement for capturing at least one image of a portion of a delivery device; a processor for processing the captured at least one image to determine a position of the apparatus relative to the drug delivery device and to determine a manner in which the apparatus should be moved in order to correctly position the apparatus on the drug delivery device; and a display for displaying an indication of the manner in which the apparatus should be moved in order to correctly position the apparatus on the drug delivery device.

19 Claims, 8 Drawing Sheets

(51) Int. Cl.
*G06K 9/62* (2006.01)
*A61M 5/31* (2006.01)

(52) U.S. Cl.
CPC ........... *A61M 2005/3126* (2013.01); *A61M 2205/215* (2013.01); *A61M 2205/3306* (2013.01); *A61M 2205/35* (2013.01); *A61M 2205/3569* (2013.01); *A61M 2205/50* (2013.01); *A61M 2205/502* (2013.01); *A61M 2205/58* (2013.01); *A61M 2205/581* (2013.01); *A61M 2205/583* (2013.01); *A61M 2205/8206* (2013.01); *G06K 2209/01* (2013.01)

(56) References Cited

U.S. PATENT DOCUMENTS

| 2012/0194671 | A1 | 8/2012 | Meiring et al. | |
|---|---|---|---|---|
| 2015/0258120 | A1* | 9/2015 | Zarnitsyn | A61K 9/0019 |
| | | | | 604/506 |

FOREIGN PATENT DOCUMENTS

| WO | WO 2013/086255 | 6/2013 | |
|---|---|---|---|
| WO | WO 2013/120777 | 8/2013 | |
| WO | WO 2014/173768 | 10/2014 | |
| WO | WO-2015187797 A1 * | 12/2015 | ........ A61M 5/14248 |

OTHER PUBLICATIONS

International Preliminary Report on Patentability in International Application No. PCT/EP2016/063323, dated Dec. 12, 2017, 8 pages.

* cited by examiner

DEVICE FOR ATTACHMENT TO A DRUG DELIVERY DEVICE

CROSS REFERENCE TO RELATED APPLICATIONS

The present application is the national stage entry of International Patent Application No. PCT/EP2016/063323, filed on Jun. 10, 2016, and claims priority to Application No. EP 15171308.8, filed in on Jun. 10, 2015, the disclosures of which are expressly incorporated herein in entirety by reference thereto.

TECHNICAL FIELD

The present disclosure relates to a device configured to assist a user in correctly positioning the device on a drug delivery device, such as an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose.

SUMMARY

A first aspect of the disclosure provides an apparatus configured to assist a user in correctly positioning the apparatus on a drug delivery device, the apparatus comprising: attachment means for attaching the apparatus to the drug delivery device; an imaging arrangement for capturing at least one image of a portion of a drug delivery device; a processor for processing the captured at least one image to determine a position of the apparatus relative to the drug delivery device and to determine a manner in which the apparatus should be moved in order to correctly position the apparatus on the drug delivery device; and a display for displaying an indication of the manner in which the apparatus should be moved in order to correctly position the apparatus on the drug delivery device.

The processor may be configured to divide each of the at least one images into a plurality of segments and to measure a luminosity of at least one of the plurality of segments. The plurality of segments may comprise a central segment and a plurality of surrounding segments and the processor may be configured to determine that the apparatus is correctly located relative to the drug delivery device when it is determined that the central segment has a luminosity below a first threshold and the surrounding segments have a luminosity exceeding a second threshold.

The processor may be configured to determine that the apparatus is correctly located relative to the drug delivery device when it is determined that the central segment has a luminosity below the first threshold and each of the plurality of surrounding segments has a luminosity exceeding the second threshold.

The processor may be configured to determine that the apparatus is correctly located relative to the drug delivery device when it is determined that the central segment has a luminosity below the first threshold and the plurality of surrounding segments have a combined luminosity exceeding the second threshold.

The processor may be configured to determine that the apparatus is not correctly located relative to the drug delivery device when it is determined that at least one of the plurality of surrounding segments has a luminosity below a third threshold. The processor may be configured, when it is determined that the apparatus is not correctly located relative to the drug delivery device, to determine the manner in which the apparatus should be moved by identifying which of the plurality of surrounding segments has a luminosity below the third threshold.

The image output from the sensor may comprise luminosity information for each image pixel. The luminosity information may be based on a grey scale output. Alternatively, the luminosity information may be based on a calculation using colour signal output. Further alternatively, the luminosity information may be based on binary image output such as black and white, e.g. after applying a binarization process.

The luminosity information may be determined by determining the number of black and/or white pixels.

The luminosity of a segment may be determined by determining the number of black and/or white pixels in the segment. Alternatively, the luminosity of a segment may be determined by the combined image output of each pixel in the segment, wherein each pixel provides luminosity information based on grey scale, based on calculation using colour signal output, or binary image output such as black and white.

The processor may be configured to: convert each captured image into a binary image; divide each binary image into a plurality of segments; and determine a number of black pixels and a number of white pixels in the plurality of segments of each binary image.

The plurality of segments may comprise a central segment and a plurality of surrounding segments and the processor may be configured to determine that the apparatus is correctly located relative to the drug delivery device when it is determined that the central segment has a number of black pixels exceeding a first threshold and the surrounding segments have a number of black pixels below a second threshold.

The processor may be configured to determine that the apparatus is correctly located relative to the drug delivery device when it is determined that the central segment has a number of black pixels exceeding the first threshold and each of the plurality of surrounding segments has a number of black pixels below the second threshold.

The processor may be configured to cause the display to display an indication that the apparatus is correctly aligned relative to the delivery device. The indication may comprise the characters "O" and "K". The indication may be a pictogram, for example showing "thumbs up" or a "check mark". The indication may comprise information that confirms to the user that the apparatus is correctly located relative to the drug delivery device.

The processor may be configured to determine that the apparatus is correctly located relative to the drug delivery device when it is determined that the central segment has a number of black pixels exceeding the first threshold and the plurality of surrounding segments have a combined number of black pixels below the second threshold.

The processor may be configured to determine that the apparatus is not correctly located relative to the drug delivery device when it is determined that at least one of the plurality of surrounding segments has a number of black pixels exceeding a third threshold.

The processor may be configured, when it is determined that the apparatus is not correctly located relative to the drug delivery device, to determine the manner in which the apparatus should be moved by identifying which of the plurality of surrounding segments has a number of black pixels exceeding the third threshold.

The plurality of segments may comprise a central segment and a plurality of surrounding segments and the processor may be configured to perform an optical character recognition process on the central segment and to determine that the apparatus is correctly located relative to the drug delivery device when it is determined that the number zero is located in the central segment.

The plurality of segments may be arranged in a quadrilateral.

The indication of the manner in which the apparatus should be moved may comprise an arrow indicated a direction in which the apparatus should be moved.

The imaging arrangement may be configured to capture at least one image of a moveable number sleeve of the drug delivery device.

The apparatus may be configured to capture the at least one image while the apparatus is being attached to the drug delivery device.

The apparatus may be configured to be moved along a longitudinal axis of the drug delivery device and to be rotated about the longitudinal axis of the drug delivery device.

The apparatus may further comprise a longitudinal extension arranged to obscure a portion of the drug delivery device external to a housing of the drug delivery device when the apparatus is correctly located relative to the drug delivery device. The portion of the drug delivery device external to the housing may be a portion of a number sleeve of the drug delivery device which is extendable from the housing.

A second aspect of the disclosure provides a method for assisting a user in correctly positioning an apparatus on a drug delivery device, the method comprising: providing means for attaching the apparatus to the drug delivery device; capturing at least one image of a portion of a drug delivery device; processing the captured at least one image to determine a position of the apparatus relative to the drug delivery device and to determine a manner in which the apparatus should be moved in order to correctly position the apparatus on the drug delivery device; and displaying an indication of the manner in which the apparatus should be moved in order to correctly position the apparatus on the drug delivery device.

BRIEF DESCRIPTION OF THE FIGURES

The figures show:
FIG. 1b shows a perspective view of some detail of the drug delivery device of FIG. 1a.

DETAILED DESCRIPTION

In the following, embodiments of the present disclosure will be described with reference to an insulin injection device. The present disclosure is however not limited to such application and may equally well be deployed with injection devices that eject other medicaments, or with other types of drug delivery devices, such as syringes, needleless injectors and inhalers.

Figure 1A:
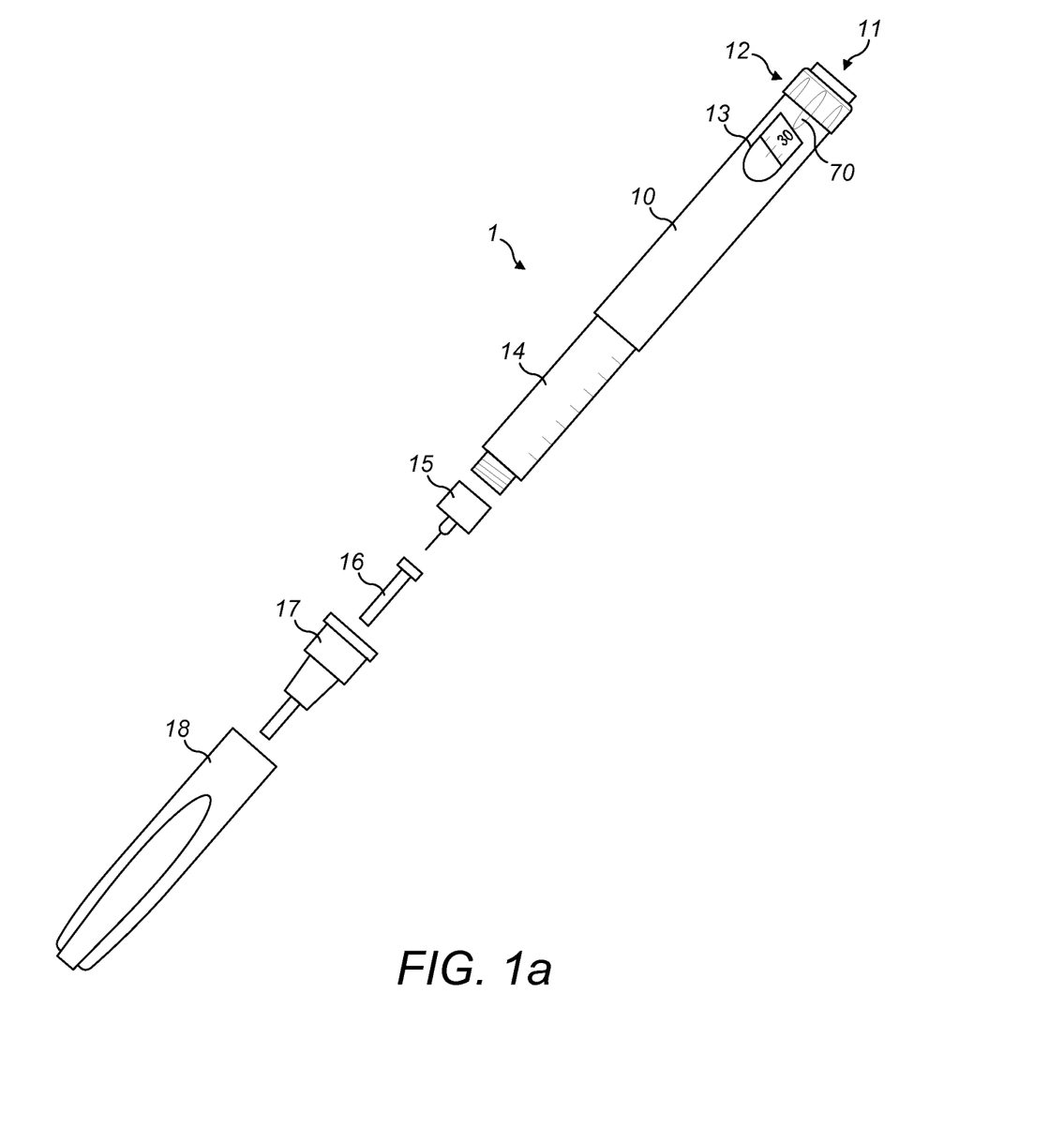
FIG. 1a is an exploded view of an drug delivery device.

FIG. 1 is an exploded view of an injection device 1 (also referred to herein as a drug delivery device), which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1. It should be noted that the selected dose may equally well be displayed differently. A label (not shown) is provided on the housing 10. The label includes information about the medicament included within the injection device, including information identifying the medicament. The information identifying the medicament may be in the form of text. The information identifying the medicament may also be in the form of a colour. The information identifying the medicament may also be encoded into a barcode, QR code or the like. The information identifying the medicament may also be in the form of a black and white pattern, a colour pattern or shading.

Turning the dosage knob 12 causes a mechanical click sound to provide acoustical feedback to a user. The numbers displayed in dosage window 13 are present on a sleeve by printing and the sleeve is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
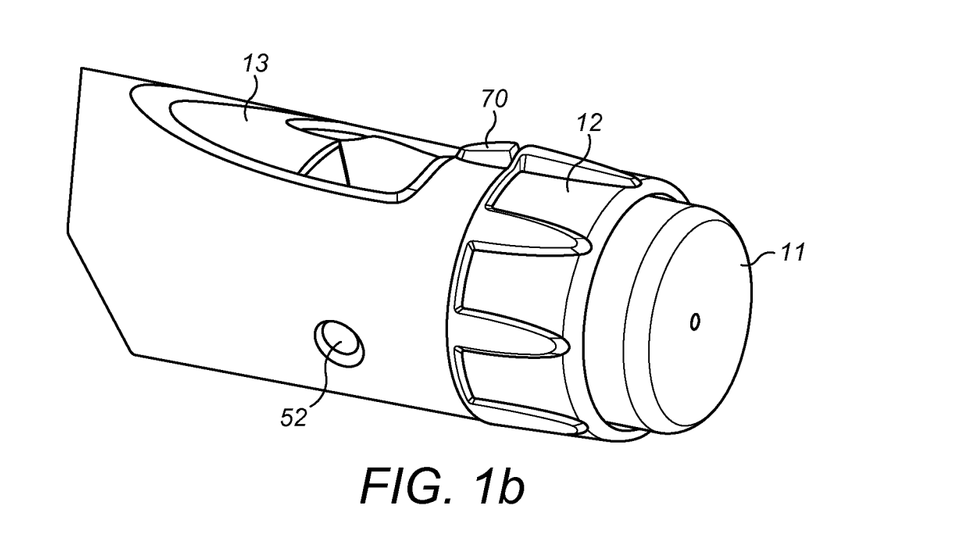

FIG. 1b is a close-up of the end of the injection device 1. The injection device has a guiding rib 70 located on the housing 10 adjacent the dosage knob 12. The injection device 1 also has two indents 52 located on the housing 10. These may be symmetrical in relation to the guiding rib 70. The guiding rib 70 and indents 52 act to secure a supplementary device (described in detail below) in the correct position on the injection device 1.

Figure 2A:
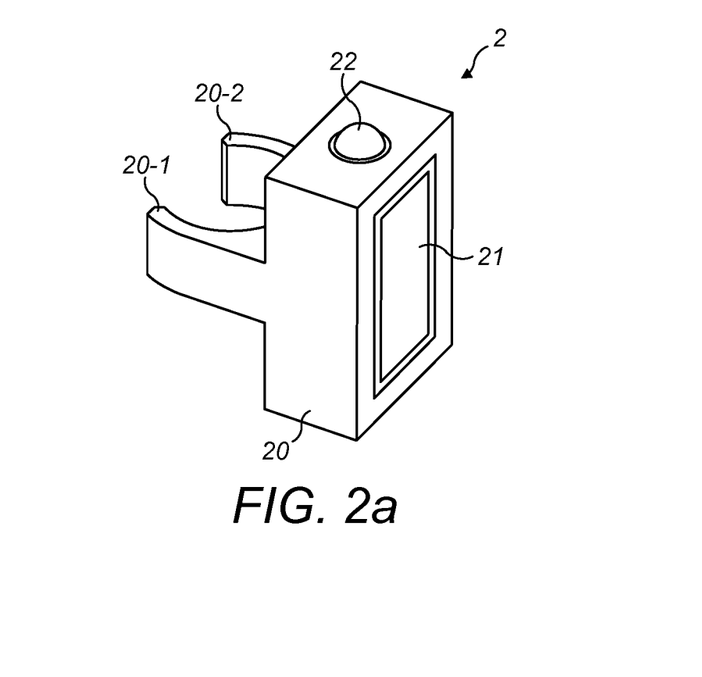
FIG. 2a is a schematic illustration of a sensor device to be releasably attached to the drug delivery device of FIGS. 1a and 1b according to an aspect of the present disclosure.

FIG. 2a is a schematic illustration of an embodiment of a supplementary device 2 (also referred to herein as sensor device 2 and device 2) to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises at least one user input transducer, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
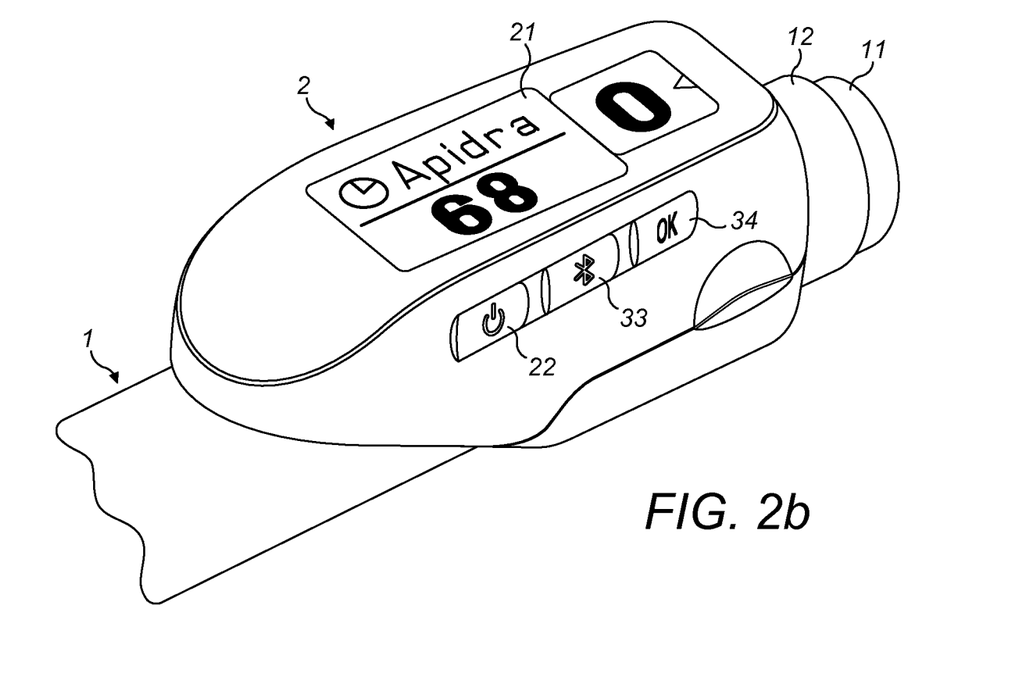
FIG. 2b is a perspective view of a sensor device to be releasably attached to the drug delivery device of FIGS. 1a and 1b according to various aspects of the present disclosure.

FIG. 2b is a schematic illustration of a second embodiment of a supplementary device 2 (also referred to herein as sensor device 2 and device 2) to be releasably attached to injection device 1 of FIG. 1. Supplementary device 2 comprises a housing 20 with a mating unit configured and embrace the housing 10 of injection device 1 of FIG. 1, so that supplementary device 2 sits tightly on housing 10 of injection device 1, but is nevertheless removable from injection device 1. The specific design and method of attachment of the device 2 to the injection device 1 is not essential to the present disclosure.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
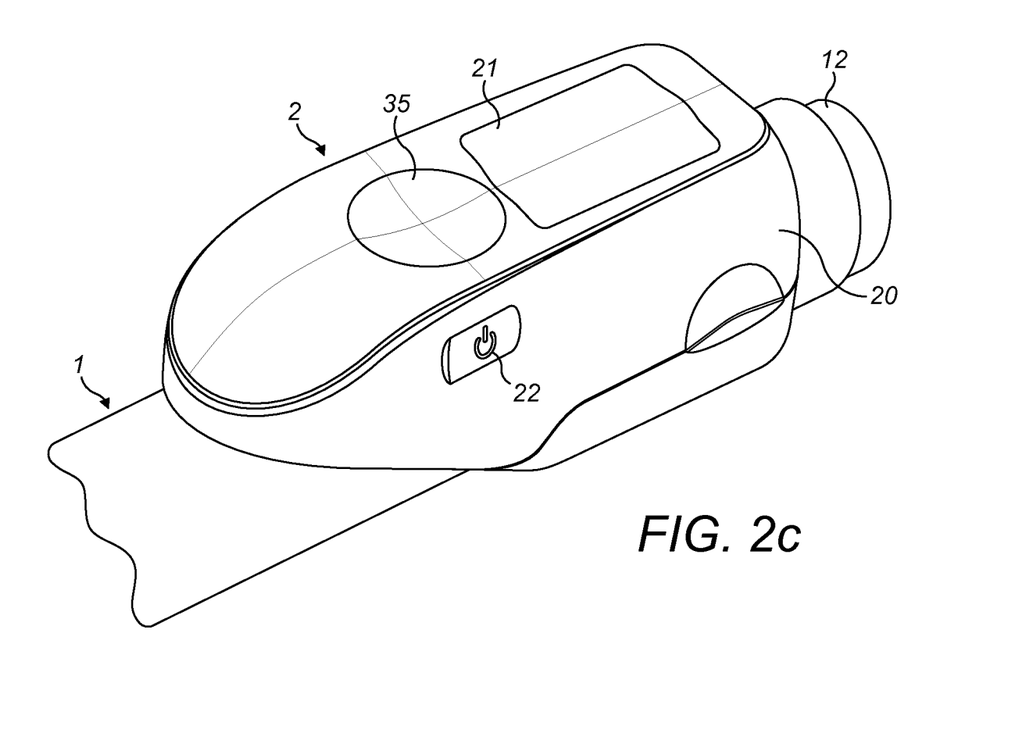
FIG. 2c is a perspective view of a sensor device to be releasably attached to the drug delivery device of FIGS. 1a and 1b according to other aspects of the present disclosure.

FIG. 2c is a schematic illustration of a third embodiment of a supplementary device 2 (also referred to herein as sensor device 2 and device 2) to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3:
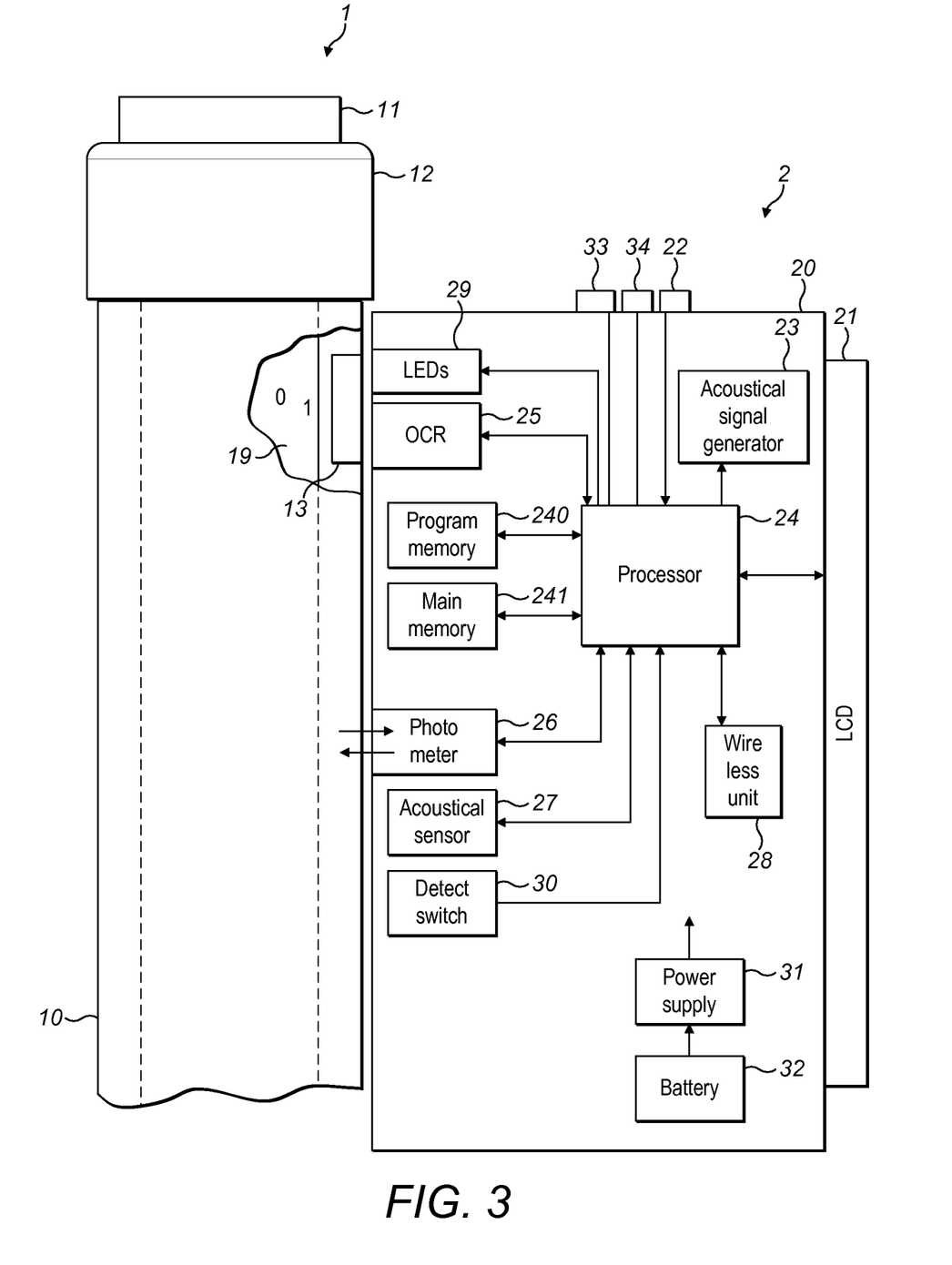
FIG. 3 is a schematic view of a sensor device attached to a drug delivery device showing components of the sensor device.

FIG. 3 shows a schematic view of the supplementary device 2 of FIG. 2a in a state where it is attached to injection device 1 of FIG. 1.

A plurality of components are contained within the housing 20 of supplementary device 2. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25 that is capable of capturing images of the dosage window 13, in which a currently selected dose is displayed (by way of numbers, characters, symbols or glyphs present on the sleeve 19 contained in injection device 1, which numbers are visible through the dosage window 13). The optical sensor 25 in supplementary device 2 is a sensor, e.g. a camera, for capturing images and providing information on the captured images to processor 24. Then processor 24 is responsible for performing optical character recognition (OCR) on the captured images. The processor 24 may be configured to perform two or more different OCR processes which each use different algorithms.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses, leading to a magnification. The magnification ratio (image size to object size ratio) may be smaller than 1. The magnification ratio may be in the range of 0.05 to 0.5. In one embodiment the magnification ration may be 0.15.

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance an expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1. A battery 32 powers the processor 24 and other components by way of a power supply 31.

The supplementary device 2 of FIG. 3 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

The injection device 1 and supplemental device 2 are configured such that the field of view of the optical sensor 25 is positioned approximately centrally over the dose window 13 when the two devices are properly aligned.

In some embodiments, due to space restrictions and the need for the numbers to be of a certain size, only even numbers are printed on the number sleeve 19. In some other embodiments, only odd numbers may be printed on the number sleeve. However, any number of units of medicament can be dialed into the injection device 1. In some alternative embodiments, every number, i.e. ascending integer numbers, may be printed on the sleeve. In these embodiments, it may be possible to dial half-unit doses into the injection device. The injection device may be limited to a maximum dialed dose of 80 units. In further alternative embodiments, only every $3^{rd}$, $4^{th}$ or $5^{th}$ number may be printed. The dose positions between the printed numbers may be indicated by tick marks. The term "printed" is used herein to indicate that the numbers are marked on the surface of the number sleeve, however the skilled person would understand that the numbers may be printed, etched, marked, attached, or otherwise made visible to the optical sensor 25 of the supplementary device 2 in a number of known ways.

The processor 24 is configured to execute an algorithm which allows the numbers (or partial numbers) visible in the field of view of the optical sensor 25 to be separated and prepared for comparison with stored templates in order to identify them. This algorithm performs an optical character recognition (OCR) process on the visible numbers and uses the results of the OCR process in order to determine accurately the dose which is currently dialed into the injection device 1. The algorithm may be embodied in software or firmware and may be stored in the program memory 240 of the supplemental device 2. The processor 24 and memory 240 storing the algorithm together may be referred to herein as a "processor arrangement".

The entire algorithm can be divided into a pre-processing part, an OCR-part, and a post-processing part, wherein each part generally involving several steps.

In the pre-processing part image data quality is assessed and improved by executing the following steps:
Defective and bad pixel correction
Light correction
Distortion and slant correction For example, an exposure control algorithm rejects pictures that are too bright or too dark and a new picture is taken with adjusted exposure parameters. The numbers may be printed on a slant for ease of recognition and positioning by a human, but may be easier to decode if this slant is removed. For the purpose of the disclosure described and claimed herein, the pre-processing is an optional feature. The OCR part of the algorithm can be designed to perform to the required standard without pre-processing of the image and/or the optical sensor 25 can be configured to produce images of sufficient quality for OCR to be performed on them directly.

In the OCR part, the image data is then further processed and at the end a recognized character is available. The OCR process comprises the steps of:
Binarization
Segmentation
Pattern matching
Position calculation The post-processing may involve various checks and the production of a result to be displayed. The post-processing comprises the following steps:
Perform sanity checks
Hysteresis calculation
Show end result on display Due to the high reliability requirements of the sensor device 2, there may in some embodiments be two OCR algorithms that are operated in parallel. The two OCR algorithms have the same input (image) and are intended to provide the same output. They both perform similar steps however the individual methods used in each step may vary. These two OCR algorithms may differ in one of the binarization, segmentation, pattern matching and position calculation steps or in more than one of these steps. Having two OCR-parts which use different methods to provide the same result increases the reliability of the entire algorithm as the data has been processed in two independent ways.

A key challenge is to implement an image capture and subsequent OCR process including segmentation into a small system that is reliably capable of recognizing numbers, characters, and/or glyphs from a display to determine a dose value. The system is battery powered, small and has limited imaging as well as processing capabilities owed to the compact design and life time requirements. A processor for this kind of device typically has a clock rate of about 100 MHz or below, a memory of up to 32 kByte RAM and 512 kb flash (these specifications are exemplary and not intended to be limiting). However, the result of the OCR process should be available in real time, meaning that the user dialing in a dose can read it from the supplemental device while dialing. A typical computation time would be about 70 ms.

The OCR system described above can only be performed with the required levels of confidence if the device 2 and injection device 1 are correct aligned and secured together. This assembly procedure may not be straightforward for all users of the devices and thus some means of assisting users in connecting the two devices is required.

Therefore, during the assembly procedure the processor 24 also controls optical sensor 25 that is capable of capturing images of a portion of the drug delivery device, for example the dosage window 13, the housing 10 of the injection device 1, or a combination thereof. In particular, during the final assembly, when device 2 and injection device 1 are correctly aligned and secured to each other, the optical sensor 25 provides images of the dosage window 13 that is obscured by the device 2 and assists the user in correctly aligning the optical sensor 25 relative to the dosage window 13.

Figure 4:
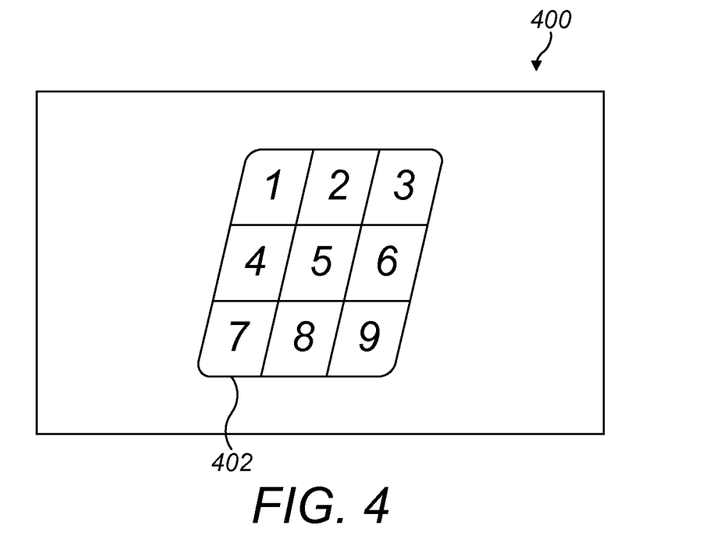
FIG. 4 is a diagrammatic illustration of the field of view of the optical sensor.

Referring now to FIG. 4, a diagrammatic illustration of the field of view 400 of the optical sensor 25 is shown. The field of view 400 has a central area which is divided into a plurality of segments 402. The segments 402 may together form any regular shape, such as a triangle, circle, oval or quadrilateral such as a square, rectangle or parallelogram. Each of the segments 402 may be the same shape and size, or alternatively one or more of the segments 402 may have a different shape and/or size.

In the embodiment depicted in FIG. 4, the segments together form a parallelogram. The central area is divided into nine segments arranged in a slanted three by three grid. The segments 402 have been numbered 1 to 9 in the manner of a telephone keypad and may be referred to individually herein by numerals 402-1 to 402-9 respectively or more generally by numeral 402. Each of the segments 402 is itself a parallelogram and are of equal size. However, it will be appreciated that in some other embodiments, the central segment 402-5 may be larger and/or of a different shape to the surrounding segments. The numbers printed on the number sleeve 19 may be printed in a slanting fashion (see FIG. 5) and therefore the device 2 may be better able to determine its position with respect to the injection device 1 if the filed of view of the optical sensor 25 is also divided into slanting segments, as shown in the Figures. However, the skilled person would appreciate that this is not essential and that square or rectangular segments could be used for both slanted and non-slanted numbers.

The division of the field of view of the optical sensor 25 into segments may be done virtually by a processor 24 which receives images from the optical sensor or may be a feature of the hardware of the optical sensor 25, for example the segments may relate to actual groups of photo sensors in the optical sensor 25.

The division of the central part of the field of view of the optical sensor 25 into segments 402 allows the optical sensor to be used while the device 2 is being attached to the injection device 1 by a user in order to assist the user in correctly positioning the device 2, as will now be explained in greater detail.

Figure 5:
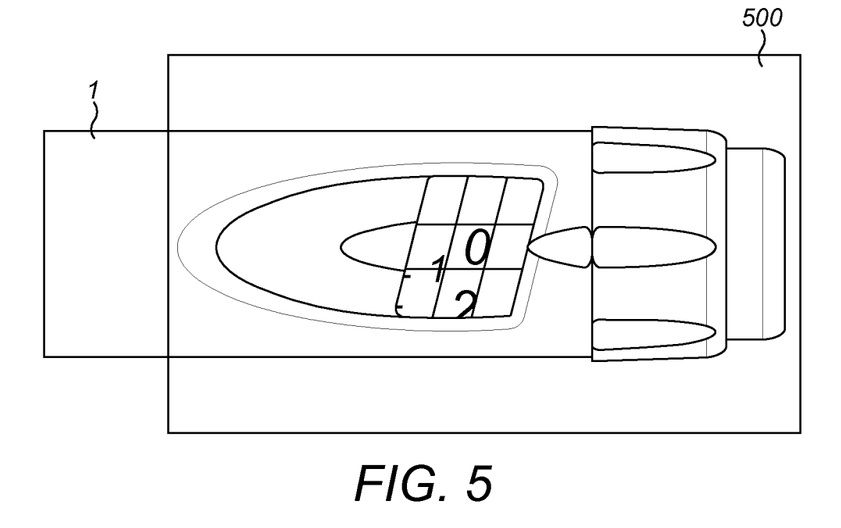
FIG. 5 is illustration of the field of view of the optical sensor when the device has been correctly positioned and attached to the injection device.
Figure 7A:
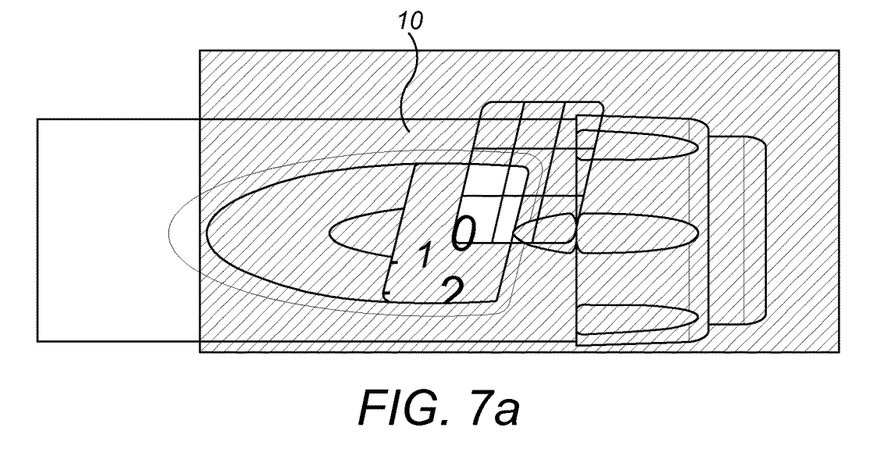
FIG. 7a shows a field of view of the optical sensor when the device has been incorrectly positioned and the housing of the injection device has a dark colour.
Figure 8:
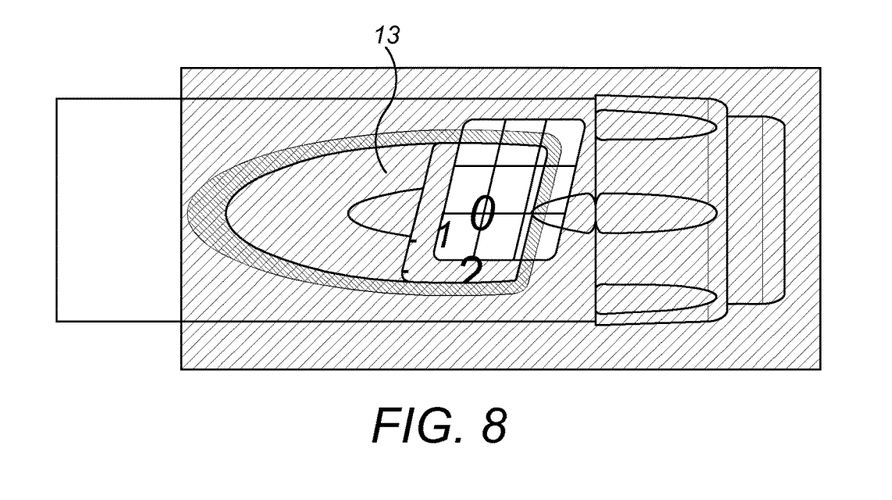
FIG. 8 shows a field of view of the optical sensor when the device has been incorrectly positioned and the housing of the injection device has a light colour.

FIG. 5 shows a field of view 500 of the optical sensor 25 when the device 2 has been correctly positioned and attached to the injection device 1. The injection device 1 is in its initial position in which no units are dialed in, and therefore the character "0" is displayed centrally in the dose window 13. When the device 2 is correctly positioned, the "0" appears in the central segment 402-5 of the plurality of segments. FIGS. 7a and 8 show further examples of a field of view of the optical sensor 25 during attachment of the device 2 to the injection device 1. In these Figures, the device is not correctly positioned on the injection device 1 and the "0" does not appear in the central segment 402-5 of the plurality of segments. The processor 24 is configured to determine the difference between the situation shown in FIG. 5 and those shown in FIGS. 7a and 8, to determine in which direction the device 2 is misaligned and to provide an indication of the manner in which the device 2 should be moved by the user in order to position it correctly. This may be achieved in several ways as will now by described.

In some embodiments, the processor 24 may use the raw image data output from the sensor 25 (i.e. a greyscale image) to assess the relative positions of the device 2 and injection device 1. The greyscale image output from the sensor 25 may contain only luminosity information for each image pixel. The processor 24 is programmed to divide the images received from the sensor 25 into segments and to measure the luminosity of one or more of these segments. In some embodiments, the luminosity of every segment is determined. Several different luminosity thresholds may be set in the software executed by the processor 24 and the processor 24 compares the measured luminosity values with these thresholds. A first luminosity threshold value is associated with the central segment 402-5. The first threshold value is set such that when the "0" is located within in the central segment 402-5, the measured luminosity value of that segment is below the threshold. In general, the dose sleeve 19 is white (or a light colour) and the numbers are printed in black ink, such that the presence of a number decreases the luminosity in the vicinity of the number. The threshold may be chosen such that if only a part of the "0" is located in the central segment 402-5, then the first luminosity threshold for that segment is exceeded. In some further embodiments, the software executed by the processor 24 may also store a lower luminosity threshold for the central segment 402-5. Clearly when the "0" is correctly located, there is some bright area in the central segment, therefore if the luminosity of the central segment 402-5 is so low that it can be deduced that the central segment is completed obscured, a determination of misaligned is made.

In some embodiments, the processor is configured to determine, on the basis of this comparison alone, whether the device 2 is correctly positioned on the injection device 1. The comparison of the luminosity value of a single segment with a single threshold can be accomplished very quickly by even a very limited microprocessor and thus the indication of whether the device 2 is misaligned or not can be returned in real time to a user.

In some other embodiments, the processor 24 also measures the luminosity of other segments in order to make any determination. For example, the processor 24 may measure the luminosity of all of the surrounding segments. In these embodiments, a second threshold value is set such that when the "0" is located within in the central segment 402-5, the measured luminosity values of the surrounding segments exceed the second threshold. This situation may be determined in at least two ways. In one method, the luminosity values for each segment may individually be compared with the second threshold to determine which of them exceed the threshold. As can be seen in FIG. 5, when the device 2 is correctly located, the majority of the surrounding segments contain an image of the (light coloured) number sleeve 19 only, and thus have a high luminosity value. Some other features, such as the numbers 1 and 2 and the tick marks, may be visible in some of the surrounding segments. These can be accounted for in a number of ways. When the device 2 is correctly positioned, the number "2" is only partly visible. The number "1" is wholly visible but is smaller (in terms of black ink area) than the other numbers. Both numbers are also likely to extend over more than one individual segment. Therefore, the second luminosity threshold may be set at a level such that the presence of these other features in some of the surrounding segments does not cause the luminosity values for those segments to fall below the second threshold. As a further safeguard against misdetection, the processor 24 may require only that the first luminosity threshold for the central segment 402-5 is exceeded and that a majority of the surrounding segments have a luminosity exceeding the second threshold, such as five or six out of the eight surrounding segments. As a modification of this first method, further luminosity threshold values may be set for specific segments where it is expected that there will be other features.

For example, the threshold values set for the lower left segment 402-7 and the lower central segment 402-8 may be lower than those set for the other surrounding segments, to account for the expected appearance of the numbers 1 and 2 in those regions. The processor 24 therefore checks the measured luminosity of every segment individually against a threshold (or several different thresholds) in order to determine whether the device 2 and injection device 1 are properly aligned.

In a second method, the luminosity values of every surrounding segment, or some selected subset of the surrounding segments, are combined and compared with the second threshold. The second threshold would be a different (much higher) value in this second method than in the first method. Combining the individual segment values, or merely treating the area surrounding the central segment 402-5 as a single segment, and comparing the result with a single threshold is less computationally intensive than comparing each segment with a threshold individually. A determination that the general area surrounding the central segment has a luminosity exceeding the second threshold combined with a determination that the central segment 402-5 has a luminosity below the first threshold will, in many circumstances, be a sufficiently robust indication that the device 2 is correctly aligned. In a modification to this method, some of the surrounding segments may not be including in the combined luminosity. For example, the lower left segment 402-7 and the lower central segment 402-8, which are expected to contain some dark features, may not be included in the combination. In this situation, the second luminosity threshold could be set at a more robust level, i.e. the remaining six segments are required to be 'brighter'.

In some other embodiments, the processor 24 converts the received raw image (greyscale) data output from the sensor 25 to a binary image of black and white pixels. The processor 24 then uses the binarized image of the field of view 400, 500 to assess the relative positions of the device 2 and injection device 1. The greyscale image output from the sensor 25 contains luminosity information for each image pixel. This luminosity is compared to a threshold to determine whether the pixel should be black or white. The processor 24 is programmed to divide the binarized image of the field of view into segments and to determine the pixel content of one or more of these segments. Each segment may comprise several hundred or more individual pixels. Analogous with the embodiments described above, the software executed by the processor may store several thresholds, expressed in terms of number of black or white pixels. A first threshold relates to the central segment 402-5. The processor 24 measures the number of black and white pixels in the binarized mage of the central segment and compares it to a first pixel threshold. The first threshold value is set such that when the "0" is located within in the central segment 402-5, the measured number of black pixels exceeds the first threshold. The threshold may be chosen such that if only a part of the "0" is located in the central segment 402-5, then the first pixel threshold for that segment is not exceeded. In some embodiments, the processor is configured to determine, on the basis of this comparison alone, whether the device 2 is correctly positioned on the injection device 1. The comparison of the pixel content of a single segment with a single threshold can be accomplished very quickly by even a very limited microprocessor and thus the indication of whether the device 2 is misaligned or not can be returned in real time to a user.

In some other embodiments, the processor 24 also measures the pixel content of other segments in order to make any determination. For example, the processor 24 may measure the pixel content of all of the surrounding segments. In these embodiments, a second threshold value is set such that when the "0" is located within in the central segment 402-5, the number of black pixels of the surrounding segments is below the second threshold. This situation may be determined in at least two ways. In one method, the number of black pixels in each segment may individually be compared with the second threshold to determine which of them are below the threshold. As can be seen in FIG. 5, when the device 2 is correctly located, the majority of the surrounding segments contain an image of the (light coloured) number sleeve 19 only, and thus have a low number of black pixels. Some other features, such as the numbers 1 and 2 and the tick marks, may be visible in some of the surrounding segments. These can be accounted for in a number of ways. When the device 2 is correctly positioned, the number "2" is only partly visible. The number "1" is wholly visible but is smaller (in terms of black ink area) than the other numbers. Both numbers are also likely to extend over more than one individual segment. Therefore, the second pixel threshold may be set at a level such that the presence of these other features in some of the surrounding segments does not cause the number of black pixels in those segments to exceed the second threshold. As a further safeguard against misdetection, the processor 24 may require only that the first pixel threshold for the central segment 402-5 is exceeded and that a majority of the surrounding segments have a number of black pixels below the second threshold, such as five or six out of the eight surrounding segments. As a modification of this first method, further pixel threshold values may be set for specific segments where it is expected that there will be other features. For example, the threshold values set for the lower left segment 402-7 and the lower central segment 402-8 may be higher than those set for the other surrounding segments, to account for the expected appearance of the numbers 1 and 2 in those regions. The processor 24 therefore checks the measured number of black pixels of every segment individually against a threshold (or several different thresholds) in order to determine whether the device 2 and injection device 1 are properly aligned.

In a second method, the number of black pixels in every surrounding segment, or some selected subset of the surrounding segments, are combined and compared with the second threshold. The second threshold would be a different (much higher) value in this second method than in the first method. Combining the individual segment values, or merely treating the area surrounding the central segment 402-5 as a single segment, and comparing the result with a single threshold is less computationally intensive than comparing each segment with a threshold individually. A determination that the general area surrounding the central segment has a number of black pixels below the second threshold combined with a determination that the central segment 402-5 has a number of black pixels exceeding the first threshold will, in many circumstances, be a sufficiently robust indication that the device 2 is correctly aligned. In a modification to this method, some of the surrounding segments may not be including in the combined black pixel value. For example, the lower left segment 402-7 and the lower central segment 402-8, which are expected to contain some dark features, may not be included in the combination. In this situation, the second pixel threshold could be set at a more robust level, i.e. the remaining six segments are required to be 'whiter'.

In some further embodiments, the generation of a binarized image of the field of view allows and optical character recognition (OCR) process to be performed. For example, after binarizing the image and dividing it into segments, the processor 24 may perform an OCR process on the central segment 402-5 and determine whether it contains a "0" as required for proper alignment. If there are any other expected features in the field of view, an OCR process may be performed to ensure that these are located where expected. Using OCR reduces the possibility of the captured image passing all of the threshold tests by chance when the device 2 is not correctly positioned.

The skilled person would also appreciate that any of the techniques described above could be used in combination to achieve a desired level of confidence in the result. For example, if a very high level of confidence was required, the processor 24 could generate a binarized image and perform OCR on the central segment 402-5 to determine that a "0" is located there. The processor could then use the raw greyscale image to determine that the luminosity of some or all of the surrounding segments is above a threshold.

As will be appreciated from the above description, as the user attached the device 2 to the injection device 1, the device 2 completely obscures the dose window 13 of the injection device. This may make it difficult to properly align the two devices, particular for a user who has poor dexterity or eyesight. Although the injection device 1 may optionally be provided with a guiding rib 70, indents 52 or some other locating feature, the detachable nature of the device 2 means that it may still be quite easy for a user to mistakenly believe that the device is correctly attached when it is in fact misaligned.

If the processor 24 determines that the device 2 is not correctly located on the injection device 1, then it executes a further algorithm to determine a manner or direction in which the two devices are misaligned. The processor 24 then controls the display unit 21 of the device to display an indication of the manner in which the device 2 should be moved in order to correctly position the apparatus on the injection device 1.

Figure 6A:
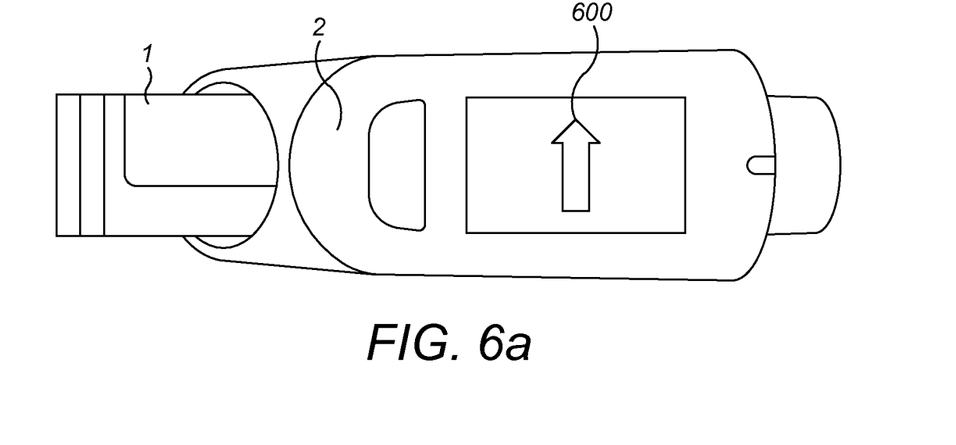
FIGS. 6a and 6b are two examples of the device mounted to the injection device incorrectly, and the resulting indication displayed.
Figure 6B:
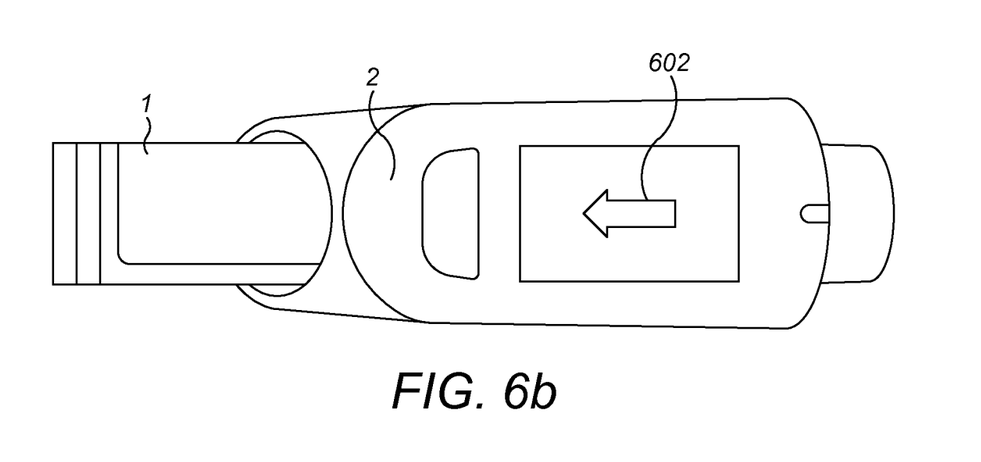

FIGS. 6a and 6b show two examples of the device 2 mounted to the injection device 1 incorrectly, and the resulting indication displayed to a user to assist them in adjusting the positioning of the device 2. In FIG. 6a, the device 2 has the correct longitudinal position with respect to the injection device 1, but an incorrect rotational position. The display unit 21 of the device 2 therefore displays and indication 600, in this case an arrow, showing the user that they should rotate the device 2 relative to the injection device 1. In FIG. 6b, the device 2 has the correct rotational position with respect to the injection device 1, but an incorrect longitudinal position. The display unit 21 of the device 2 therefore displays an arrow 602 showing the user that they should slide or otherwise move the device 2 longitudinally relative to the injection device 1.

Figure 7B:
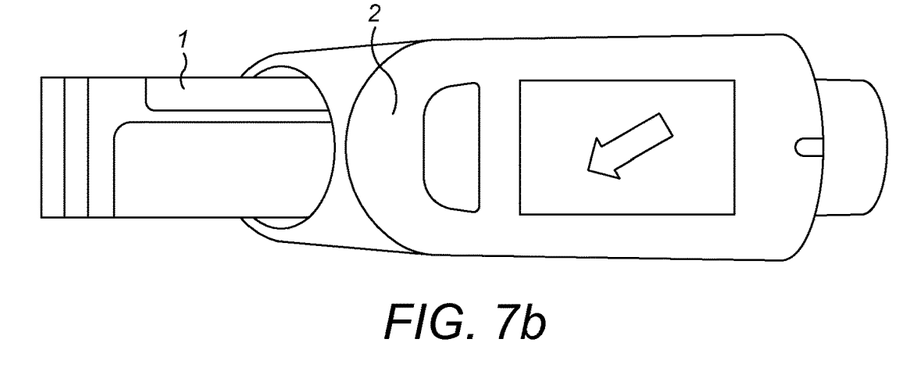
FIG. 7b is a device displaying an indication of the manner in which the device should be moved when the device is misaligned as shown in FIG. 7a or FIG. 8.

FIGS. 7a, 7b and 8 illustrate further examples of the operation of the device 2 with two different types of injection device 1. The different types of injection device may for example contain different types of medication. The main body of the injection device 1 may have a different overall colour as an indicator of the type of medicament contained therein. For the purposes of these embodiments, it will be assumed that the processor 24 uses the luminosity values obtained from the greyscale sensor image, however it will be appreciated that the pixel content method or some combination of the two methods is equally applicable.

In FIG. 7a, the housing 10 of the injection device 1 has a dark colour. The device 2 is misaligned with respect to the injection device 1 such that it is too far longitudinally towards the button end of the injection device and rotational too far clockwise when viewed from the button end of the injection device 1. The result of this is that the upper and right hand segments of the field of view of the sensor record dark areas (of the pen body 10 and optionally the dosage knob 12). The processor 24 therefore determines luminosity levels for segments 1-3, 6 and 9 that are below the second threshold. The processor may or may not determine that the luminosity of the central segment 402-5 is below the first threshold. In any case, the processor subsequently determines that the device 2 is misaligned towards the button end of the injection device along the longitudinal direction and clockwise (as viewed from the button end) with respect to the dose window 13.

In some embodiments, in order to improve the confidence level of the misalignment detection, the processor 24 may be configured to use two or more successive images in its determination. As a user attaches the devices together, the luminosity values for each of segments will change and the processor 24 may compare successive images to more accurately determine the past relative positions of the devices and the manner in which they are currently misaligned. Alternatively or in addition, if the confidence level in the direction of misalignment is too low, the display unit 21 may show a general message or instruction such as "device misaligned" or "move device", to indicate to the user that the devices are not correctly aligned. Once the user has moved the device 2 a further attempt to determine the direction of misalignment can be made.

Having determined the direction of misalignment, the processor 24 controls the display unit 21 to display an indication of the manner in which the device 2 should be moved in order to correctly position the device on the injection device 1, as shown in FIG. 7b. This indication comprises an arrow pointing towards the bottom left of the display unit 21. The arrow may point in the direction in which the processor 24 has determined that the device 2 should be moved, or may occupy one of a number of discreet orientations, in which case the closest orientation to the actual direction is chosen. The processor 24 continuously re-performs the misalignment detection described above such that the arrow changes orientation in real time as the user moves the device 2, thus assisting the user in correctly positioning the devices.

In FIG. 8, the housing 10 of the injection device 1 has a light colour. However, the dose window 13 has a dark border region. The device 2 is again misaligned with respect to the injection device 1 such that it is too far longitudinally towards the button end of the injection device and rotational too far clockwise when viewed from the button end of the injection device 1. The result of this is that the upper and right hand segments of the field of view of the sensor record some dark areas (corresponding to the dark border of the dose window) and some light areas (corresponding to the housing). In the case of a light coloured housing, the luminosity threshold levels for the surrounding segments may need to be different. The photometer 26 may allow the processor to determine an optical property of the housing 10 of injection device 1, and select the thresholds appropriately.

The algorithm may also be more dependent on determining that the "0" is located in the central segment 402-5. For example, the processor may use both upper and lower luminosity thresholds for the central segment 402-5, or alternatively perform OCR or a form of pattern recognition on the central segment, when the housing 10 of the injection device 1 has a light colour.

In the case depicted in FIG. 8, the processor 24 determines luminosity levels for segments 1-3, 6 and 9 that are below the second threshold. The processor may also determine that the luminosity of the central segment 402-5 is above the first threshold. In any case, the processor subsequently determines that the device 2 is misaligned towards the button end of the injection device along the longitudinal direction and clockwise (as viewed from the button end) with respect to the dose window 13. The processor 24 then controls the display unit 21 to display the same indication as shown in FIG. 7b.

The arrow type indicator may be a static arrow (although the orientation of the arrow may change) or it may be more active. For example, the size of the arrow may change, getting smaller as the amount of misalignment decreases. Alternatively or in addition, the colour of the arrow may change. A 'traffic light' system could be used where the arrow changes from red to amber to green as the amount of misalignment decreases. The arrow may be animated, for example moving back and forth in the direction in which movement is required. The arrow may also be accompanied by some aural instruction or feedback, such as a verbal description of the movement required or beeps which may increase in frequency or pitch as the amount of misalignment decreases.

It will be appreciated that the arrow shown in FIGS. 6a, 6b and 7b is only one example of an indicator which could be used. For example, the display may instead contain crosshairs and a target location or some other pair of objects which must be made to overlap or intersect.

When the user has successfully aligned the two devices a feedback to this effect may be provided. For example, the arrow may disappear to be replaced by some confirmatory message or graphic such as a 'tick'. This may also be accompanied by an aural confirmation. If the user attempts to operate the device 2 or the injection device 1 while the devices are not correctly aligned, a warning message or graphic may be displayed on the display unit 21. This may be accompanied by an aural warning.

Figure 9A:
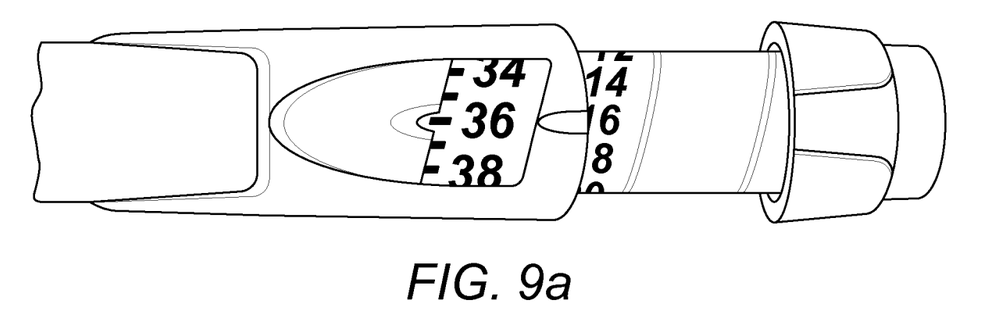
FIG. 9a is an injection device with dose dialed in showing position of numbers on dial extension.

Another operational issue encountered by some users of the device 2 is that as the dose sleeve 19 extends from the housing 10 during dialing, some numbers printed on the sleeve become visible beyond the edge of the housing. This situation is illustrated in FIG. 9a. In this Figure, a user has dialed in 36 units to the injection device 1 such that the number 36 appears centrally in the dosage window 13. However, numbers printed on the part of the number sleeve 19 which has extended out from the housing 10 are also visible. In user trials, it has been observed that some users read the numbers printed on this part of the number sleeve 19, rather than the number shown in the dosage window 13. For example, a user may read the dialed dose as '16', rather than '36', which can lead to an overdose being delivered. A situation like this could occur in particular when the device 2 is not correctly positioned on the drug delivery device 1. For example, the device 2 may not be correctly aligned relative to device 1 in the longitudinal direction.

This problem can be addressed when using the sensor device 2 described herein. In most designs the device 2 is configured to attach at or near the edge of the housing 10, but does not overlap with the dosage knob 12, in order to allow a user to continue to easily set and deliver doses without being obstructed by the presence of the device 2.

Therefore, in most designs, the problem described above regarding the numbers visible on the extended part of the number 19 may still occur.

The upper part or face of the device 2 may therefore be modified to incorporate a longitudinal extension (or spoiler) which causes the extended part of the number sleeve 19 to be obscured.

Figure 9B:
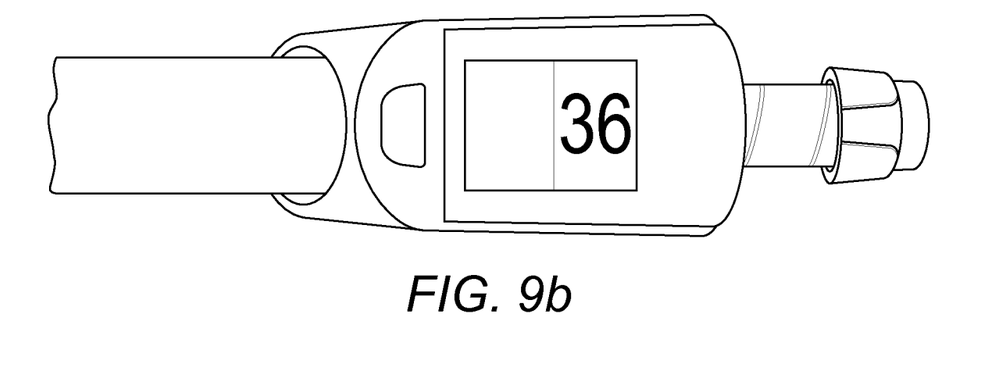
FIGS. 9b and 9c are two examples of a device having a rear longitudinal extension, mounted to the injection device.
Figure 9C:
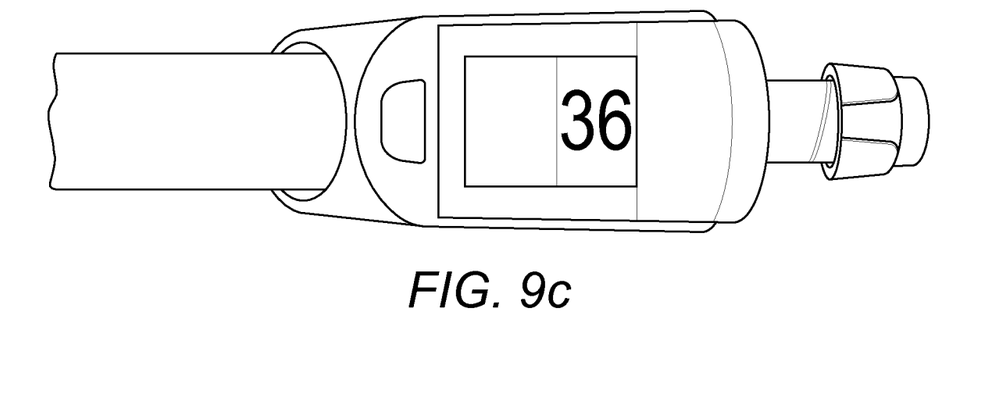

FIGS. 9b and 9c show two examples of how this can be accomplished. In FIG. 9b, an extension is provided to part of the main housing 20 of the device 2. This extension may be secured to the housing 20 after the housing has been moulded or alternatively it may be integrally moulded with the housing 20. Only the top face, i.e. the face of the device 2 having the display, has the longitudinal extension. This means that the device 2 does not obstruct the dosage knob 12 such that doses can be dialed in and delivered normally. However, when the injection device 1 with the device 2 attached is viewed by a user, at least a portion of the number sleeve 19 which has extended from the housing 10 is obscured from view.

In FIG. 9c, the longitudinal extension is an extension of the display unit 21 of the device 2. The display unit may comprise an LCD and a transparent cover. This cover may be extended to form the longitudinal extension. In either of the embodiments shown, the extension may have an approximate width of 3-4 mm, which has been found sufficient to obscure at least the closest part of the extended number sleeve 19 to the housing 10 of the injection device 1.

The extended part of the LCD cover may be frosted or otherwise made less transparent. Providing an extended LCD cover (as in FIG. 9c) may be an easier implementation of the extension to manufacture than the housing extension (as in FIG. 9b) as the LCD cover may be a completely separate part from the housing 20 of the device 2, which is then attached towards the end of the manufacturing process. In addition, the extended LCD cover is further away from the injection device 1 than an extension of the main housing 20, and therefore the chance that the extension would hinder the operation of the injection device 1 is reduced.

The invention claimed is:

1. An apparatus configured to assist a user in correctly positioning the apparatus on a drug delivery device, the apparatus comprising:
   an attachment component comprising a mating unit, the attachment component configured to attach the apparatus to the drug delivery device;
   an optical sensor configured to capture at least one image of a portion of the drug delivery device;
   a processor configured to process the captured at least one image to determine a position of the apparatus relative to the drug delivery device and to determine a manner in which the user should move the apparatus in order to correctly position the apparatus on the drug delivery device, wherein the manner includes a direction to align a specific part of the apparatus with a marking on the drug delivery device; and
   a display configured to display an indication of the manner in which the apparatus should be moved in order to correctly position the apparatus on the drug delivery device.

2. The apparatus according to claim 1, wherein the processor is configured to divide each of the at least one image into a plurality of segments and to measure a luminosity of at least one of the plurality of segments.

3. The apparatus according to claim 2, wherein the plurality of segments comprise a central segment and a plurality of surrounding segments, and wherein the processor is configured to determine that the apparatus is correctly located relative to the drug delivery device when it is determined that the central segment has a first luminosity below a first threshold and the plurality of surrounding segments have a second luminosity exceeding a second threshold.

4. The apparatus according to claim 3, wherein the processor is configured to determine that the apparatus is correctly located relative to the drug delivery device when it is determined that the central segment has the first luminosity below the first threshold and each of the plurality of surrounding segments has the second luminosity exceeding the second threshold.

5. The apparatus according to claim 3, wherein the processor is configured to determine that the apparatus is correctly located relative to the drug delivery device when it is determined that the central segment has the first luminosity below the first threshold and the plurality of surrounding segments have a combined luminosity exceeding the second threshold.

6. The apparatus according to claim 2, wherein the processor is configured to determine that the apparatus is not correctly located relative to the drug delivery device when it is determined that at least one of the plurality of surrounding segments has a luminosity below a third threshold.

7. The apparatus according to claim 6, wherein the processor is configured, when it is determined that the apparatus is not correctly located relative to the drug delivery device, to determine the manner in which the apparatus should be moved by identifying which of the plurality of surrounding segments has a luminosity below the third threshold.

8. The apparatus according any of claim 2, wherein the processor is configured to measure luminosity by:
converting each captured image into a binary image;
dividing each binary image into a plurality of segments; and
determining a number of black pixels and a number of white pixels in the plurality of segments of each binary image.

9. The apparatus according to claim 8, wherein the plurality of segments are arranged in a quadrilateral.

10. The apparatus according to claim 1, wherein the optical sensor is configured to capture at least one image of a moveable number sleeve of the drug delivery device.

11. The apparatus according to claim 1, wherein the apparatus is configured to capture the at least one image while the apparatus is being attached to the drug delivery device.

12. The apparatus according to claim 1, wherein the apparatus further comprises a longitudinal extension arranged to obscure a portion of the drug delivery device external to a housing of the drug delivery device when the apparatus is correctly located relative to the drug delivery device.

13. The apparatus according to claim 12, wherein the portion of the drug delivery device external to the housing is a portion of a number sleeve of the drug delivery device which is extendable from the housing.

14. The apparatus according to claim 1, wherein the drug delivery device comprises a cartridge comprising a medicament.

15. A method for assisting a user in correctly positioning an apparatus on a drug delivery device, the method comprising:
capturing at least one image of a portion of a delivery device;
processing the captured at least one image to determine a position of the apparatus relative to the drug delivery device and to determine a manner in which the user should move the apparatus in order to correctly position the apparatus on the drug delivery device, wherein the manner includes a direction to align a specific part of the apparatus with a marking on the drug delivery device; and
displaying an indication of the manner in which the apparatus should be moved in order to correctly position the apparatus on the drug delivery device.

16. The method of claim 15, wherein processing the captured at least one image comprises dividing each of the at least one images into a plurality of segments and to measure a luminosity of at least one of the plurality of segments.

17. The method of claim 16, wherein the plurality of segments comprises a central segment and a plurality of surrounding segments.

18. The method of claim 17, wherein processing the captured at least one image comprises determining that the apparatus is correctly located relative to the drug delivery device when the central segment has a luminosity below a first threshold and the surrounding segments have a luminosity exceeding a second threshold.

19. The method of claim 17, wherein processing the captured at least one image comprises determining that the apparatus is not correctly located relative to the drug delivery device when at least one of the plurality of surrounding segments has a luminosity below a third threshold.

\* \* \* \* \*

UNITED STATES PATENT AND TRADEMARK OFFICE
CERTIFICATE OF CORRECTION

PATENT NO. : 10,786,627 B2
APPLICATION NO. : 15/579801
DATED : September 29, 2020
INVENTOR(S) : Stephan Riedel and Alexander Allerdings Page 1 of 1

It is certified that error appears in the above-identified patent and that said Letters Patent is hereby corrected as shown below:

In the Specification

Column 1, Line 10, delete "in on" and insert -- on --

In the Claims

Column 19, Line 13, Claim 8, delete "any of" and insert -- to --

Signed and Sealed this
Twenty-second Day of December, 2020

Andrei Iancu
*Director of the United States Patent and Trademark Office*